United States Patent [19]

Sherer

[11] Patent Number: 4,507,604
[45] Date of Patent: Mar. 26, 1985

[54] FLOWABLE MATERIAL MEASURING APPARATUS

[76] Inventor: Roger L. Sherer, Box 2453, Great Falls, Mont. 59403

[21] Appl. No.: 467,038

[22] Filed: Feb. 16, 1983

[51] Int. Cl.³ .............................................. G01N 27/00
[52] U.S. Cl. .................................. 324/71.1; 198/502; 222/40
[58] Field of Search ............... 324/71.1, 71.4; 222/36, 222/40, 55, 63; 33/123; 73/861.73, 861.75; 198/502, 670, 671

[56] References Cited

U.S. PATENT DOCUMENTS

| | | | |
|---|---|---|---|
| 1,203,167 | 10/1916 | Woolson | 198/670 |
| 1,773,816 | 8/1930 | Lea | 73/861.73 |
| 2,860,420 | 11/1958 | Denman, Jr. et al. | 33/123 |
| 3,258,165 | 6/1966 | Guyer | 222/63 |
| 4,203,513 | 5/1980 | Scheppele | 198/502 |

Primary Examiner—Michael J. Tokar
Assistant Examiner—Kevin D. O'Shea
Attorney, Agent, or Firm—Arthur L. Urban

[57] ABSTRACT

Apparatus for measuring the quantity of flowable particulate material passing through a conduit; the apparatus including a mounting portion, a flowable material contacting portion, a sensing portion, a circuitry portion and a quantity determining portion; the mounting portion including a support bracket, a transversely disposed bulkhead section affixed to the bracket adjacent the entry end of the apparatus; the flowable material contacting portion including a baffle extending from the bracket adjacent the entry end of the apparatus, the baffle having one end pivotally connected to the bracket, the baffle being pivotable away from the entry end of the apparatus; the sensing portion including mechanically actuatable voltage varying mechanism, the voltage varying mechanism being mounted on the bracket adjacent the pivotal connection of the baffle with the bracket, the voltage varying mechanism being operatively connected to the baffle; the circuitry portion including a converter converting voltage values into periodic electrical pulses, a pulse adapter interfacing the periodic pulses from the converter; the quantity determining portion including a programmable information processor receiving the periodic pulses from the adapter, programming mechanism connected to the information processor for entering information therein, and a display responsive to the information processor.

11 Claims, 4 Drawing Figures

FLOWABLE MATERIAL MEASURING APPARATUS

This invention relates to a novel measuring apparatus and more particularly relates to a new apparatus for measuring quantities of flowable material.

Throughout history, people having measured quantities of a wide variety of different materials and substances. Some of these measurements have involved the determination of volume by filling a container of a particular size. Also, the weight of substances was determined through the use of a balance scale.

The above methods still are in use today for many measuring operations. Measuring containers now have standardized volumes. The balance scale has been replaced by scales that allow the weight to be determined more quickly.

While the above procedures have proven successful through the years, they are not satisfactory in all situations. Since they require individual determinations, they only are useful where one or a few measurements are required in a short period of time.

Furthermore, the above methods are not suitable where there is a continuous flow of material. The continuous flowing material may be a liquid or a solid material that is flowable due to the particulate nature of the substance.

The above methods can be utilized only if the flow is stopped periodically so increments can be measured. Although stopping the flow may be acceptable in some situations, in other cases it may be completely unsatisfactory. An example of such an unsatisfactory situation is the measuring of particulate materials such as grain moving through a conduit.

The transfer of grain and similar materials from harvesting machinery or a bin to a truck or a different bin generally involves very large quantities of material and periodic stoppage of the flow can seriously slow the transfer rate. Since grain is a relatively low cost material, slowing the transfer rate can significantly increase expenses and substantially reduce profits. Thus, there is a need for a device to measure continuously flowing grain and similar products.

It has been proposed to position a movable baffle in a conduit and to measure the deflection of the baffle as the material flows therethrough. In one device, the deflection is measured by having the baffle move a rheostat. The rheostat powers a motor which drives a clock mechanism through a combination of gears.

While the concept of employing a movable baffle in the path of the flowing material may have merit, the proposed device creates a number of serious problems. Since a significant amount of current is required to power the motor, a considerable amount of heat is generated. Thus, if the grain transferring operation lasts for a significant period of time, the components will overheat causing the accuracy of the device to be deleteriously affected as well as possibly damaging the device.

Another problem with the proposed device is calibrating the device. A sample of grain is passed through the device, the grain is measured and the clock appropriately set. Then, additional samples of grain are passed through the device and the calibration refined. These steps are repeated until the desired accuracy is achieved by trial and error. These steps can take a considerable period of time for each of the many different crops and moisture contents.

Once the device has been calibrated, there still is the problem of maintaining the calibration. The dust in the grain will tend to slow the mechanical movements employed. Thus, it may be necessary to recalibrate the device at frequent intervals.

An additional difficulty in maintaining the calibration is that the machinery on which the device is mounted frequently is moved from one location to another. For example, a combine including this device would be moved over a field as the grain is being harvested. Since the field is not perfectly smooth, the device is subjected to vibration and shock which can adversely affect the calibration. These conditions greatly increase the necessity for frequent recalibration.

A further problem with the device is the lag time of the components. This effect can cause the device to be inaccurate if there are sudden changes in the flow rate.

From the above discussion, it is clear that present and past methods of measuring flowing materials leave much to be desired. Thus, there is a need for a new and improved apparatus which eliminates the shortcomings of previous devices.

The present invention provides a novel apparatus for measuring quantities of flowable particulate material. The apparatus of the invention provides a high degree of accuracy over long periods of use. The apparatus can be calibrated quickly and easily. The necessity for recalibration is minimized. The apparatus can be operated continuously for significant periods without adversely affecting the apparatus or its calibration.

The apparatus of the present invention can be used by persons with limited mechanical or electrical skills or experience. Only a minimum of instruction is required for efficient use. The apparatus is durable in construction and has a long useful life with a minimum of maintenance.

The apparatus of the invention is simple in design and relatively inexpensive. The apparatus can be fabricated from commercially available components. Conventional industrial manufacturing techniques and procedures can be employed in its fabrication using semi-skilled labor.

These and other benefits and advantages of the novel apparatus for the present invention will be apparent from the following description and the accompanying drawings in which.

Figure 1:
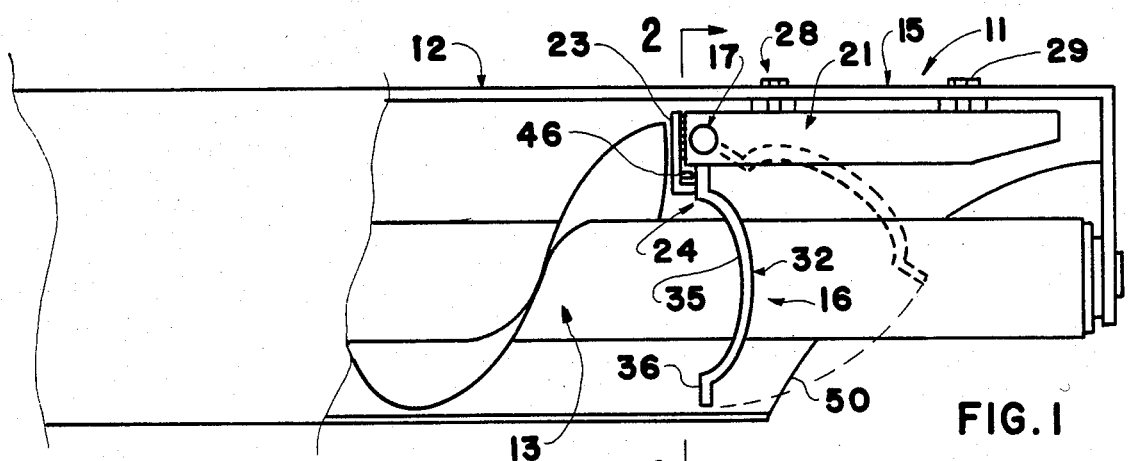
FIG. 1 is a side view partially in section of one form of the measuring apparatus of the invention mounted in a conduit.

As shown in the drawings, one form of the novel measuring apparatus 11 is mounted in a conduit 12 which includes an auger 13. The apparatus 11 measures the quantity of flowable particulate material such as grain through the conduit 12. The apparatus 11 includes a mounting portion 15, a flowable material contacting portion 16, a sensing portion 17, a circuitry portion 18 and a quantity determining portion 19.

The mounting portion 15 of the measuring apparatus 11 of the invention includes a support bracket 21. Advantageously, the bracket 21 includes a U-shaped channel member 22. A transversely disposed bulkhead section 23 is affixed to the bracket 21 adjacent the entry end 24 of the apparatus.

Mounting means 26 including openings 27 are disposed along the length of the bracket 21. Fastener means 28 including bolts 29 are employed to secure the bracket 21 to the sidewall 30 of conduit 12.

The flowable material contacting portion 16 of the measuring apparatus 11 includes baffle means 32. The baffle 32 extends from bracket 21 at a point adjacent the entry end 24 of the apparatus. The baffle 32 has one end pivotally connected to the bracket 21, preferably through a shaft 33. The baffle 32 is pivotable away from the entry end 24 of the apparatus.

The baffle 32 advantageously has a generally U-shaped configuration with a central opening extending from the free end 34 thereof. This opening accommodates a shaft of an auger 13 disposed within conduit 12. Preferably, the baffle 32 includes a semi-cylindrical section 35 along its length. Advantageously, the baffle includes a flat section 36 at least at the free end 34 of the baffle remote from the pivotal connection. The pivotal connection of the baffle 32 with respect to the bracket 21 preferably is closely adjacent to the bulkhead section 23.

The sensing portion 17 of the apparatus 11 includes mechanically actuatable voltage varying means 37 such as potentiometer 38. The voltage varying means 37 is mounted on the bracket 21 at a point adjacent the pivotal connection of the baffle 32 with the bracket. The voltage varying means 37 is operatively connected to the baffle 32.

Figures 2, 3:
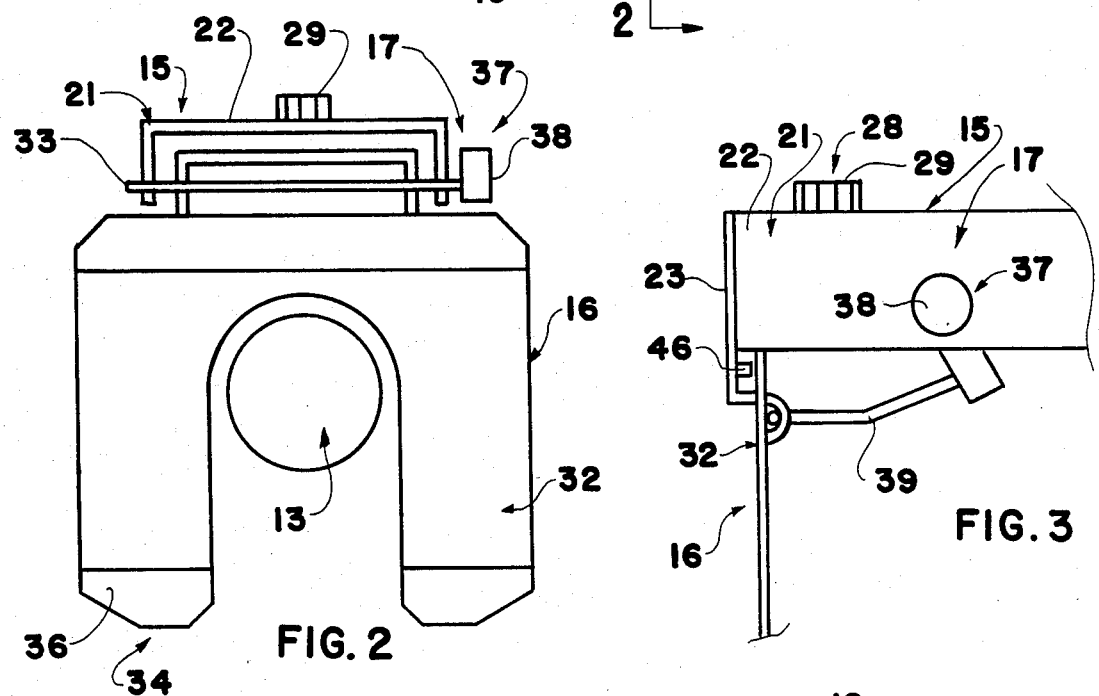
FIG. 2 is a sectional view of the apparatus shown in FIG. 1 taken along line 2—2 thereof.
FIG. 3 is a fragmentary side view of another form of the apparatus of the invention.
Figure 4:
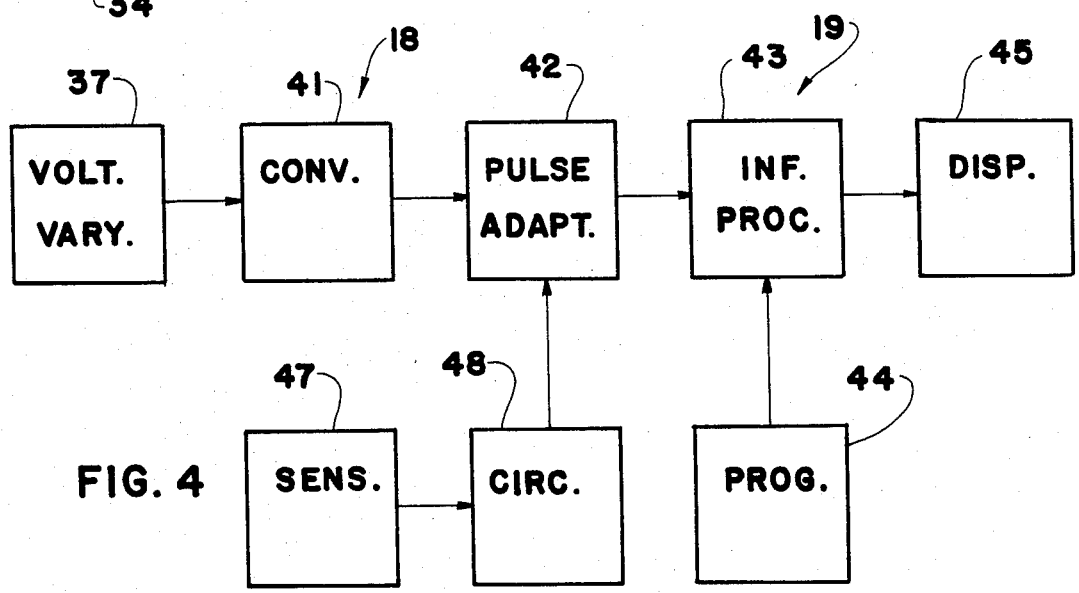
FIG. 4 is a schematic illustration of one form of circuitry of the apparatus of the invention.

Advantageously, as shown in FIG. 1, the voltage varying means 37 is mounted closely adjacent to the pivotal connection of the baffle 32 and preferably on the shaft 33. Alternatively, the voltage varying means 37 may be mounted on the bracket 21 at a point spaced from the pivotal connection. In this configuration, the voltage varying means may be operatively connected to the baffle through a linkage means 39 as shown in FIG. 3.

The circuitry portion 18 of the apparatus 11 of the invention includes converter means 41. The converter means 41 is connected electrically to the voltage varying means 37. The converter 41 changes the voltage values from the voltage varying means into periodic electrical pulses.

Pulse adapter means 42 is connected electrically to the converter 41. The pulse adapter receives periodic pulses from the converter and interfaces them for transmission to quantity determining portion 19.

The quantity determining portion 19 of the measuring apparatus 11 includes information processing means 43. The information processing means 43 is programmable, that is, includes a memory. The information processing means 43 which is connected electrically to the adapter means 42 receives the periodic pulses therefrom.

Programming means 44 is connected to the information processing means 43. The programming means 44 which may be a series of dial switches, a keyboard, etc. providing for the entering of information into the processing means 43. Display means 45 which preferably is a digital display, is responsive to the information processing means 43.

The circuitry portion 18 also may include baffle actuatable switch means 46. The switch means 46 can be connected electrically to an electronic gate that is interposed between the converter and the adapter. The switch means 46 reactivates the circuitry portion 18 when material is flowing through the conduit 12.

In place of the switch means 46, the quantity determining portion 19 may include means for adjusting the sensing level of the circuitry and quantity determining portions 18 and 19 respectively to activate the apparatus 11 only when material is flowing through conduit 12.

The apparatus 11 also preferably includes means 47 for sensing the rotation of a shaft member (not shown). This shaft member can be an axle, drive shaft, etc. of a vehicle or other machinery in which the apparatus is employed. For example, such machinery may be a combine in which the apparatus measures the quantity of grain being transferred to a truck or storage bin.

Employing the above sensing means 47 with circuitry 48 transmitting pulses to the information processing means 43 provides capability for determining information that coordinates with the quantities of grain measured.

The circuitry portion 18 and the quantity determining portion 19 ordinarily are located separate from the material contacting portion 16 and the sensing portion 17. These portions may be incorporated into a single unit if desired.

The circuitry and quantity determining portions 18 and 19 may be fabricated from integrated solid state components and integrated circuit chips. Also, it may be advantageous with some installations to employ prefabricated microprocessors that are commercially available and modify them to include the special components such as the voltage to pulse converter.

While the above description discusses the primary components of the circuitry and quantity determining portions, other components can be included to provide refinements. For example, it may be desirable to use more readily available components and to modify them with buffers, counters and the like. Also, it may be advantageous to employ inverters, etc. to eliminate contact bounce and other adverse effects.

In the use of the measuring apparatus 11 of the present invention, the apparatus is mounted in a conduit 12. As shown in the drawings, the apparatus 11 is affixed to the top of conduit 12 including auger 13. The apparatus is located so the baffle 32 is adjacent the opening 50 of the conduit.

The apparatus is mounted in position by securing bracket 21 to the top of the conduit with bolts 29. The apparatus 11 then is connected electrically to the circuitry portion 18 which is located separately from the portions 15–17 mounted in the conduit. The apparatus now is ready for use.

The auger 13 is actuated causing grain to move through the conduit 12 and out the opening 50 at the end thereof. As the grain passes the apparatus 11, the grain pushes against the baffle 32 causing it to deflect backwardly to the right.

The degree of deflection of the baffle 32 is sensed by potentiometer 38 which is mounted on shaft 33. As the baffle changes position, the voltage passing through the potentiometer also changes in value.

The converter 41 of the circuitry portion 18 which is connected to the potentiometer 38 converts the voltage values into periodic pulses, the frequency of which is directly proportional to the voltage passing through the potentiometer.

The periodic pulses from the converter 41 then pass to the adapter 42 which interfaces them for transmission to the information processing means 43. The information processor 43 previously has been programmed through programming means 44 so the quantity of grain flowing through the conduit can be determined and displayed on means 45. Thus, an operator of the auger is informed of the quantity of grain delivered.

The apparatus 11 can be calibrated simply and quickly by passing grain through the conduit 12 and past the apparatus so the information regarding the quantity is entered into information processor 43. The grain then is measured by hand and the quantity entered into the information processor through programming means 44. The apparatus 11 automatically is calibrated through the information processor 43 and is ready for use in a single step.

Where the apparatus 11 of the invention is employed with machinery such as a combine (not shown), it may be desired also to determine other information regarding the harvest in addition to the quantity of grain. This can be accomplished with the apparatus 11 by mounting sensing means 47 on an axle of the combine.

The means 47 senses the rotation of the axle and thus the distance traveled by the combine. The pulses generated by the sensor 47 are transmitted by appropriate circuitry 48 to the information processing means 43. The information processor 43 can be programmed by programming means 44 to determine distance traveled, acres harvested, yield per acre and similar information.

The above description and the accompanying drawings show that the present invention provides a novel apparatus for measuring flowing particulate materials. The apparatus can be calibrated quickly and easily. Recalibration is minimized with the apparatus of the invention. The apparatus provides a high degree of accuracy even after much use. The apparatus can be operated continuously for extended periods of time without deterioration of components or accuracy.

The apparatus of the present invention can be operated efficiently by persons with limited mechanical and/or electrical aptitude or experience after only a minimum of instruction. The apparatus is durable in construction and requires little, if any, maintenance.

The apparatus of the invention is simple in design and can be manufactured relatively inexpensively. Commercially available materials and components can be utilized in its fabrication employing conventional manufacturing procedures and semi-skilled labor.

It will be apparent that various modifications can be made in the particular measuring apparatus described in detail above and shown in the drawings within the scope of the invention. The size, configuration and arrangement of components can be changed to meet specific requirements. For example, the configuration of the baffle can be different. Also, the mounting bracket can be of another design. These and other changes can be made in the measuring apparatus provided the functioning and operation thereof are not adversely effected. Therefore, the scope of the invention is to be limited only by the following claims.

What is claimed is:

1. Apparatus for measuring the quantity of flowable particulate material passing through a conduit; said apparatus including a mounting portion, a flowable material contacting portion, a sensing portion, a circuitry portion and a quantity determining portion; said mounting portion including a support bracket, a transversely disposed bulkhead section affixed to said bracket adjacent the entry end of said apparatus, mounting means disposed along the length of said bracket, fastener means capable of securing said bracket to said conduit; said flowable material contacing portion including baffle means extending from said bracket adjacent the entry end of said apparatus, said baffle means having one end pivotally connected to said bracket, said baffle means being pivotably away from the entry end of said apparatus; said sensing portion including mechanically actuatable voltage varying means, said voltage varying means being mounted on said bracket adjacent said pivotal connection of said baffle means with said bracket, said voltage varying means being operatively connected to said baffle means; said circuitry portion including converter means connected electrically to said voltage varying means, said converter means converting voltage values into periodic electrical pulses, pulse adapter means connected electrically to said converter means, said adapter means interfacing said periodic pulses from said converter means; said quantity determining portion including programmable information processing means connected electrically to said adapter means, said information processing means receiving said periodic pulses from said adapter means, programming means connected to said information processing means for entering information therein, and display means responsive to said information processing means.

2. Measuring apparatus according to claim 1 wherein said bracket includes a U-shaped channel member.

3. Measuring apparatus according to claim 1 wherein said baffle means has a generally U-shaped configuration with a central opening extending from the free end thereof.

4. Measuring apparatus according to claim 1 wherein said baffle means includes a semi-cylindrical section along its length.

5. Measuring apparatus according to claim 1 wherein said baffle means includes a flat section at least at the free end thereof remote from said pivotal connection.

6. Measuring apparatus according to claim 1 wherein said pivotal connection of said baffle means with said bracket is closely adjacent to said bulkhead section.

7. Measuring apparatus according to claim 1 wherein said voltage varying means is disposed on a shaft pivotally connecting said baffle means with said bracket.

8. Measuring apparatus according to claim 1 wherein said voltage varying means is spaced from said pivotal connection of said baffle means with said bracket, and said voltage varying means is operatively connected to said baffle means through linkage means.

9. Measuring apparatus according to claim 1 wherein said voltage varying means includes a potentiometer.

10. Measuring apparatus according to claim 1 wherein said circuitry portion includes baffle actuatable switch means.

11. Measuring apparatus according to claim 1 wherein said sensing means includes means for sensing the rotation of a shaft member and said circuitry portion includes means transmitting pulses to said quantity determining portion.

* * * * *